US012733881B2

(12) United States Patent
Yamashita et al.

(10) Patent No.: US 12,733,881 B2
(45) Date of Patent: Sep. 15, 2026

(54) SPHYGMOMANOMETER, BLOOD PRESSURE MEASUREMENT METHOD, AND COMPUTER-READABLE RECORDING MEDIUM

(71) Applicant: OMRON HEALTHCARE CO., LTD., Muko (JP)

(72) Inventors: Shingo Yamashita, Kyoto (JP); Yukiya Sawanoi, Kyoto (JP); Mika Ezoe, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 849 days.

(21) Appl. No.: 17/745,183

(22) Filed: May 16, 2022

(65) Prior Publication Data

US 2022/0273246 A1 Sep. 1, 2022

Related U.S. Application Data

(63) Continuation of application No. PCT/JP2020/042299, filed on Nov. 12, 2020.

(30) Foreign Application Priority Data

Nov. 26, 2019 (JP) ................................ 2019-213489

(51) Int. Cl.
*A61B 5/00* (2006.01)
*A61B 5/022* (2006.01)

(52) U.S. Cl.
CPC ............ *A61B 5/7275* (2013.01); *A61B 5/022* (2013.01); *A61B 5/742* (2013.01)

(58) Field of Classification Search
CPC ....... A61B 5/022; A61B 5/681; A61B 5/7275; A61B 5/742; G16H 40/63
See application file for complete search history.

(56) References Cited

U.S. PATENT DOCUMENTS 9,351,689 B2 * 5/2016 Sawanoi ............ A61B 5/02225
2006/0047204 A1 * 3/2006 Chen ...................... A61B 5/022 600/490

(Continued)

FOREIGN PATENT DOCUMENTS

CN 101779952 A * 7/2010
JP H02-55033 A 2/1990

(Continued)

OTHER PUBLICATIONS

Fujiwara et al. Comparison of different schedules of nocturnal home blood pressure measurement using an information/communication technology-based device in hypertensive patients. J Clin Hypertens (Greenwich). Nov. 2018;20(11):1633-1641. doi: 10.1111/jch.13407. Epub Oct. 23, 2018. (Year: 2018).*

(Continued)

*Primary Examiner* — Aurelie H Tu
*Assistant Examiner* — Andrew E Hoffpauir
(74) *Attorney, Agent, or Firm* — Oliff PLC

(57) ABSTRACT

A sphygmomanometer includes a first type schedule, a second type schedule, and a control unit that disables one of first blood pressure measurement scheduled based on the first type schedule and second blood pressure measurement scheduled based on the second type schedule or changes a start time of the scheduled first blood pressure measurement or a start time of the scheduled second blood pressure measurement to provide idle time between the first blood pressure measurement and the second blood pressure measurement in a case where a time zone of the scheduled first blood pressure measurement and a time zone of the scheduled second blood pressure measurement at least partially overlap with each other or in a case where a time difference between the time zone of the first blood pressure measure- (Continued)

ment and the time zone of the second blood pressure measurement is equal to or less than a predetermined value.

10 Claims, 12 Drawing Sheets

(56) References Cited

U.S. PATENT DOCUMENTS

| | | | | |
|---|---|---|---|---|
| 2010/0280395 | A1* | 11/2010 | Lin | A61B 5/0002 600/485 |
| 2013/0226014 | A1* | 8/2013 | Liu | A61B 5/0235 600/498 |
| 2014/0213919 | A1* | 7/2014 | Poon | A61B 5/7405 600/509 |
| 2019/0365245 | A1 | 12/2019 | Tsutsumi et al. | |
| 2019/0380624 | A1 | 12/2019 | Ota et al. | |
| 2020/0258029 | A1* | 8/2020 | Jung | G06Q 10/1097 |

FOREIGN PATENT DOCUMENTS

| | | | | | |
|---|---|---|---|---|---|
| JP | H05-68669 | A | | 3/1993 | |
| JP | 2002-165765 | A | | 6/2002 | |
| JP | 2003061919 | A | * | 3/2003 | G16H 40/63 |
| JP | 2006-102260 | A | | 4/2006 | |
| JP | 2008311998 | A | * | 12/2008 | |
| WO | 2012/018029 | A1 | | 2/2012 | |
| WO | 2018/168797 | A1 | | 9/2018 | |
| WO | 2018/168799 | A1 | | 9/2018 | |
| WO | WO-2019082494 | A1 | * | 5/2019 | A61B 5/0015 |

OTHER PUBLICATIONS

WO2019082494A1 English Translation (Year: 2019).*

JP 2008311998 A English Translation (Year: 2008).*

Eguchi et al. What is the optimal interval between successive home blood pressure readings using an automated oscillometric device? J Hypertens. Jun. 2009;27(6):1172-7. doi: 10.1097/hjh.0b013e32832a6e39. (Year: 2009).*

Asayama et al. International Expert Group of Nocturnal Home Blood Pressure. Nocturnal blood pressure measured by home devices: evidence and perspective for clinical application. Journal of Hypertension 37(5):p. 905-916, May 2019. | DOI: 10.1097/HJH.0000000000001987 (Year: 2019).*

Hartmann "Veroval wrist blood pressure monitor", Technical Data Sheet, Sep. 13, 2018 (Year: 2018).*

Kollias A, Ntineri A, Stergiou GS. Association of night-time home blood pressure with night-time ambulatory blood pressure and target-organ damage: a systematic review and meta-analysis. J Hypertens. Mar. 2017;35(3):442-452. doi: 10.1097/HJH.0000000000001189. PMID: 27930440. (Year: 2017).*

Yano, Y., Kario, K. Nocturnal blood pressure and cardiovascular disease: a review of recent advances. Hypertens Res 35, 695-701 (2012). https://doi.org/10.1038/hr.2012.26 (Year: 2012).*

Kario et al., Nighttime Blood Pressure Measured by Home Blood Pressure Monitoring as an Independent Predictor of Cardiovascular Events in General Practice. Hypertension. Jun. 2019;73(6):1240-1248. doi: 10.1161/HYPERTENSIONAHA.118.12740. PMID: 31006331; PMCID: PMC6510323. (Year: 2019).*

JP2003061919A English Translation (Year: 2003).*

CN 101779952 A English Translation (Year: 2010).*

Jan. 26, 2021 International Search Report issued in International Patent Application No. PCT/JP2020/042299.

* cited by examiner

SPHYGMOMANOMETER, BLOOD PRESSURE MEASUREMENT METHOD, AND COMPUTER-READABLE RECORDING MEDIUM

CROSS-REFERENCE TO RELATED APPLICATIONS

This is a continuation application of International Application No. PCT/JP2020/042299, with an International filing date of Nov. 12, 2020, which claims priority of Japanese Patent Application No. 2019-213489 filed on Nov. 26, 2019, the entire content of which is hereby incorporated by reference.

TECHNICAL FIELD

The present invention relates to a sphygmomanometer, and more particularly to a sphygmomanometer having a nighttime (sleep) blood pressure measurement mode. Further, the present invention relates to a blood pressure measurement method for measuring blood pressure by such a sphygmomanometer. Further, the present invention relates to a computer-readable recording medium storing a program for causing a computer to execute such a blood pressure measurement method.

BACKGROUND ART

In general, blood pressure measurement is preferably performed in the same time zone every day so that blood pressure of the subject is reliably checked. In order to satisfy this requirement, Patent Document 1 (JP 2006-102260 A) discloses a sphygmomanometer that performs blood pressure measurement at a preset time. With the sphygmomanometer described above, for example, blood pressure measurement can be automatically performed even during the nighttime when the subject is sleeping.

SUMMARY OF THE INVENTION

A result of blood pressure measurement during nighttime is important information in examining the cardiovascular disease risk of the subject. For this reason, it is preferable to obtain a stable blood pressure value as a result of blood pressure measurement during nighttime. It is known that a stable blood pressure value can be calculated by performing blood pressure measurement during nighttime at a predetermined time (for example, 2:00 AM) or at a certain time (for example, after four hours) after sleeping. In contrast, in a case where the sleeping time of the subject greatly changes, for example, in a case where the subject is a shift worker and switches going to sleep at 10:00 PM and going to sleep at 10:00 AM every week, there is a case where blood pressure measurement cannot be performed at a predetermined time. Therefore, blood pressure measurement during nighttime is preferably performed at both a predetermined time and a predetermined time interval from a time of going to sleep so that various lifestyles of various subjects can be supported as much as possible.

In contrast, if times at which the subject sleeps vary, blood pressure measurement performed at the predetermined time and blood pressure measurement performed at a predetermined time interval from the time at which the subject goes to sleep overlap, and the blood pressure measurement may be continuously performed. In a case where a method of blood pressure measurement is, for example, an oscillometric method in which a measured site of the subject is temporarily pressed by a blood pressure measuring cuff so that blood pressure is measured, if the blood pressure measurement is continuously performed, the physical burden on the subject becomes excessively large, and there is a possibility that sleep is disturbed.

The present invention has been made to solve the above-described problem, and it is an object of the present invention to provide a sphygmomanometer and a blood pressure measurement method by which a situation in which blood pressure measurement is continuously performed when blood pressure measurement performed at a predetermined time overlaps with or is close to blood pressure measurement performed at a predetermined time interval from a time of going to sleep can be avoided. Further, an object of the present invention is to provide a computer-readable recording medium storing a program for causing a computer to execute such a blood pressure measurement method.

In order to achieve the object, a sphygmomanometer of the present disclosure has a nighttime blood pressure measurement mode for automatically starting blood pressure measurement according to a predetermined schedule, wherein the schedule includes a first type schedule in which blood pressure measurement is started at a predetermined time and a second type schedule in which blood pressure measurement is started at a predetermined time interval from a designated time, the sphygmomanometer comprising:

a control unit that disables one of first blood pressure measurement scheduled based on the first type schedule and second blood pressure measurement scheduled based on the second type schedule or changes one of a start time of the first blood pressure measurement and a start time of the second blood pressure measurement to provide idle time between the first blood pressure measurement and the second blood pressure measurement in a case where a time zone of the first blood pressure measurement and a time zone of the second blood pressure measurement at least partially overlap with each other or in a case where a time difference between the time zone of the first blood pressure measurement and the time zone of the second blood pressure measurement is equal to or less than a predetermined value.

In the present description, the “first type schedule” and the “second type schedule” included in the “schedule” define start times of blood pressure measurement (which usually requires for about one minute to two minutes). The “time interval” of the blood pressure measurement in the “second type schedule” means an interval between the “designated time” and a start time of certain blood pressure measurement or an interval between a start time of certain blood pressure measurement and a next start time, and is assumed to have the same meaning as a cycle.

The “designated time” means a time designated by the user (typically, the subject) of the sphygmomanometer, and may be, for example, a time when the user inputs an instruction to make a transition to the nighttime blood pressure measurement mode to the sphygmomanometer.

The “time zone” of the blood pressure measurement refers to time (for example, in the oscillometric method in which a measured site of the subject is temporarily pressed by a blood pressure measuring cuff to measure blood pressure, it usually takes about one minute to two minutes) in which the blood pressure measurement is actually performed.

In another aspect, a blood pressure measurement method of the present disclosure is performed in a nighttime blood pressure measurement mode for automatically starting blood pressure measurement according to a predetermined schedule, wherein the schedule includes a first type schedule in which blood pressure measurement is started at a predetermined time and a second type schedule in which blood pressure measurement is started at a predetermined time interval from a designated time, the blood pressure measurement method comprising:

setting the first type schedule and the second type schedule, and disabling one of first blood pressure measurement scheduled based on the first type schedule and second blood pressure measurement scheduled based on the second type schedule or changing one of a start time of the first blood pressure measurement and a start time of the second blood pressure measurement to provide idle time between the first blood pressure measurement and the second blood pressure measurement in a case where the time zone of the first blood pressure measurement and the time zone of the second blood pressure measurement at least partially overlap with each other or in a case where a time difference between the time zone of the first blood pressure measurement and the time zone of the second blood pressure measurement is equal to or less than a predetermined value.

In still another aspect, a computer-readable recording medium of the present disclosure is a computer-readable recording medium non-transitorily storing a program for causing a computer to execute the blood pressure measurement method.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

MODE(S) FOR CARRYING OUT THE INVENTION

Hereinafter, an embodiment of a wrist-type sphygmomanometer according to the present invention will be described with reference to the accompanying drawings.

Wrist-Type Sphygmomanometer

Figure 1:
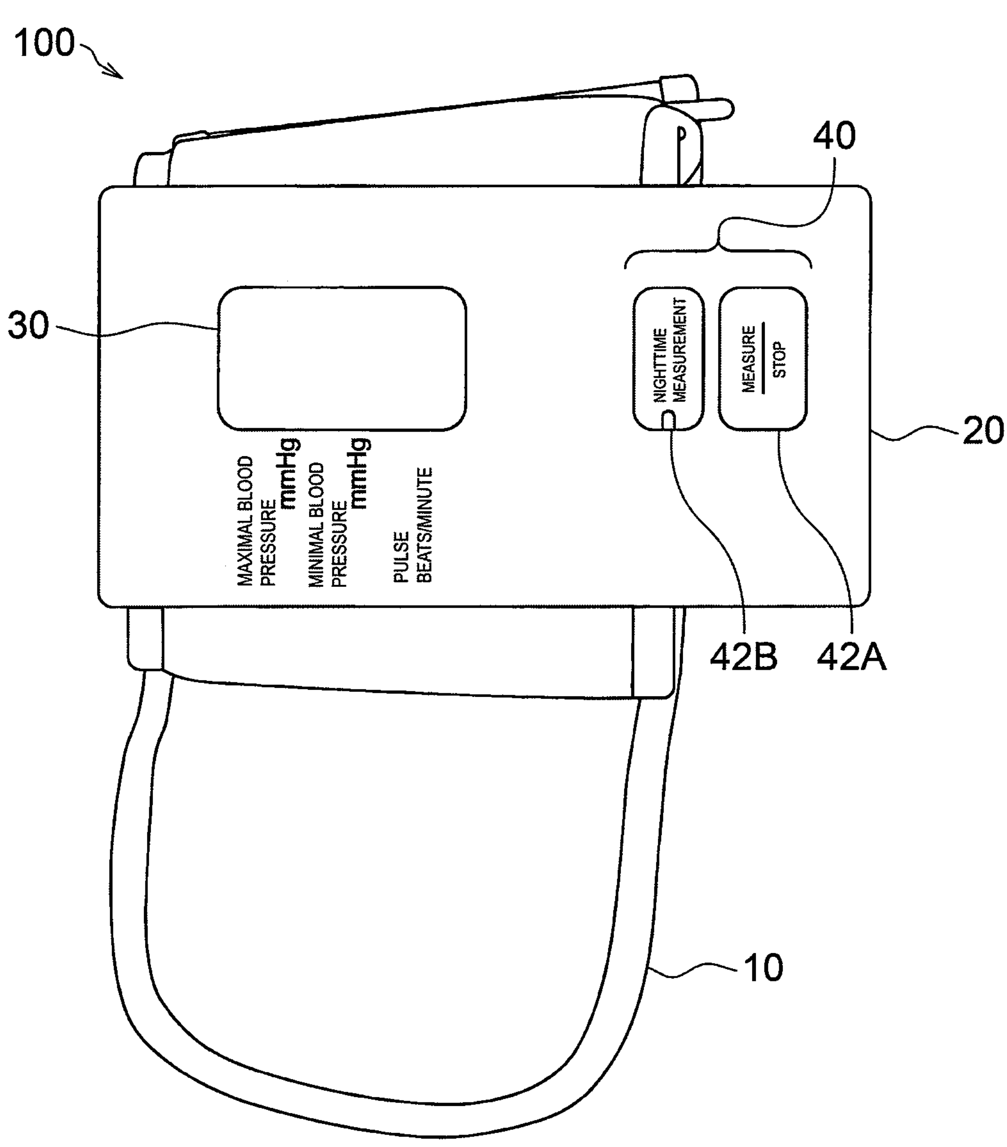
FIG. 1 is a schematic diagram of a wrist-type sphygmomanometer according to an embodiment of the present invention.

FIG. 1 shows a schematic configuration of a wrist-type sphygmomanometer (hereinafter, referred to as the "sphygmomanometer") 100 according to an embodiment of the present invention. As will be described later, the sphygmomanometer 100 has a normal blood pressure measurement mode in which blood pressure measurement is started immediately after a blood pressure measurement switch is turned on, and a nighttime blood pressure measurement mode in which blood pressure measurement is started at a predetermined time or a predetermined time interval from a designated time.

Configuration of Wrist-Type Sphygmomanometer

As illustrated in FIG. 1, the sphygmomanometer 100 includes a cuff 10 for blood pressure measurement wound around a measurement target site of a subject and a sphygmomanometer main body 20 integrally attached to the cuff 10.

Figure 2:
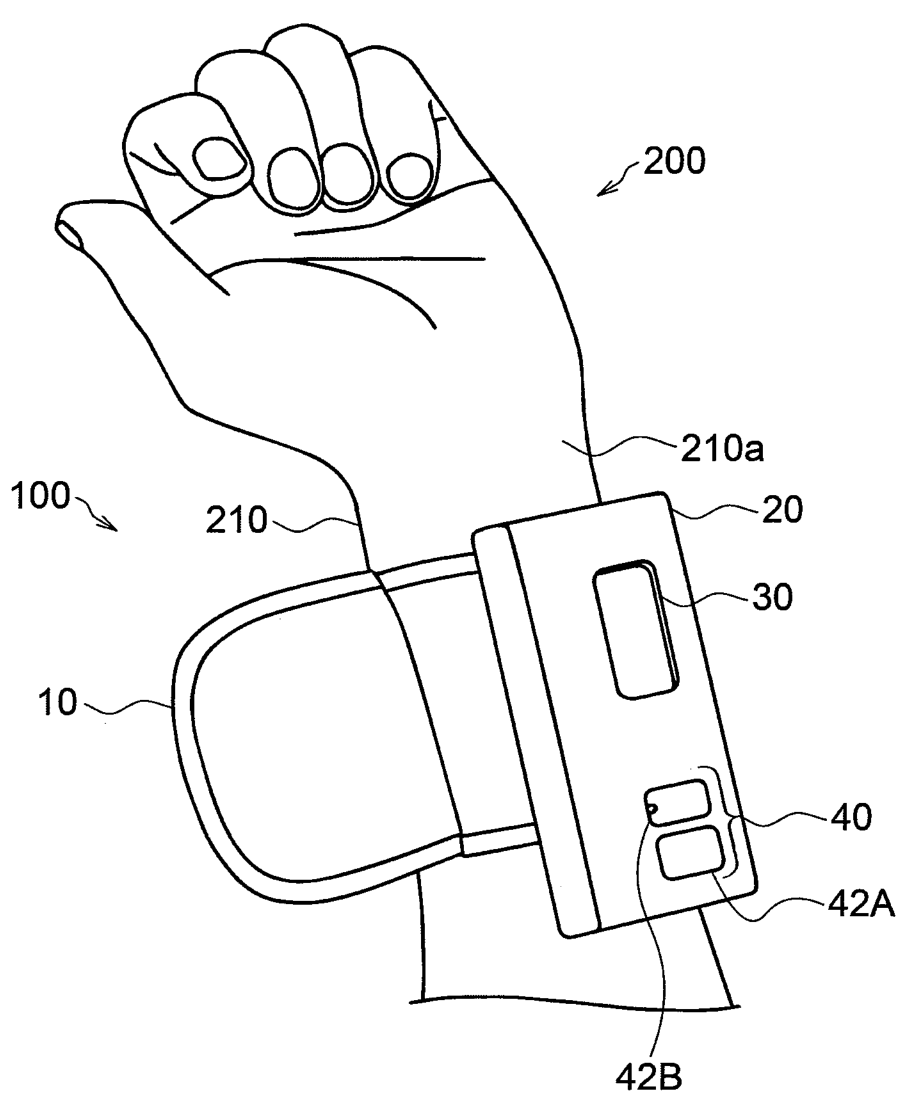
FIG. 2 is a schematic view illustrating a state in which the wrist-type sphygmomanometer illustrated in FIG. 1 is wound around a left wrist.

As illustrated in FIG. 2, the sphygmomanometer 100 according to the embodiment is a wrist-type sphygmomanometer. Therefore, the cuff 10 has an elongated band-like shape so as to be wound around a left wrist 210 of a subject 200, for example. The cuff 10 contains an air bag (see FIG. 3) for compressing the left wrist 210. Note that, in order to always maintain the cuff 10 in an annular shape, a curler (not illustrated) having appropriate flexibility may be provided in the cuff 10.

The sphygmomanometer main body 20 is integrally attached to a substantially central portion in a longitudinal direction of the cuff 10 having a band shape. In an embodiment, a portion to which the sphygmomanometer main body 20 is attached is supposed to correspond to a palmar surface (surface on the palm side) 210*a* of the left wrist 210.

The sphygmomanometer main body 20 has a flat and substantially rectangular parallelepiped shape along an outer peripheral surface of the cuff 10, and is formed to be small and thin so as not to disturb sleep of the subject 200. Further, a corner portion connecting an upper surface (surface appearing in FIG. 1) of the sphygmomanometer main body 20 and a side surface surrounding the upper surface is chamfered in a curved shape.

As illustrated in FIG. 1, a display 30 forming a display screen and an operation unit 40 for inputting an instruction from the subject 200 are provided on an upper surface on the side farthest from the left wrist 210 of an outer surface of the sphygmomanometer main body 20.

In the embodiment, the display 30 includes a liquid crystal display (LCD), and is configured to display predetermined information, for example, a maximal blood pressure (unit; mmHg), a minimal blood pressure (unit; mmHg), a pulse (units; beats per minute), and also winding determination of the cuff 10 described later in accordance with a control signal from a central processing unit (CPU) 110 described later. Note that the display 30 may be either an organic EL display or a light emitting diode (LED).

The operation unit 40 has a plurality of buttons or switches operated by the subject 200. In the embodiment, the operation unit 40 includes a blood pressure measurement switch 42A for the subject 200 to input a blood pressure measurement instruction in the normal blood pressure measurement mode, and a nighttime measurement switch (mode operation unit) 42B for the subject 200 to input a blood pressure measurement instruction in the nighttime blood pressure measurement mode. The blood pressure measurement switch 42A functions as a switch that stops blood pressure measurement being executed when the switch is pressed during the blood pressure measurement.

In description below, "normal blood pressure measurement" refers to blood pressure measurement started immediately after the blood pressure measurement switch 42A is turned on. Further, in description below, "nighttime blood pressure measurement" means blood pressure measurement automatically performed according to a predetermined schedule after a blood pressure measurement instruction is input through the nighttime measurement switch 42B, and is performed, for example, during sleep of the subject 200. The blood pressure measurement performed according to a predetermined schedule is, for example, blood pressure measurement performed at a set time such as 1:00, 2:00, or 3:00 in the middle of the night, or blood pressure measurement performed at, for example, two-hour intervals after the nighttime measurement switch 42B is pressed.

In the embodiment, both the blood pressure measurement switch 42A and the nighttime measurement switch 42B are momentary type (self-return type) switches, and are configured to be turned on only while being pushed down, and to be returned to an off state when being released.

Figure 3:
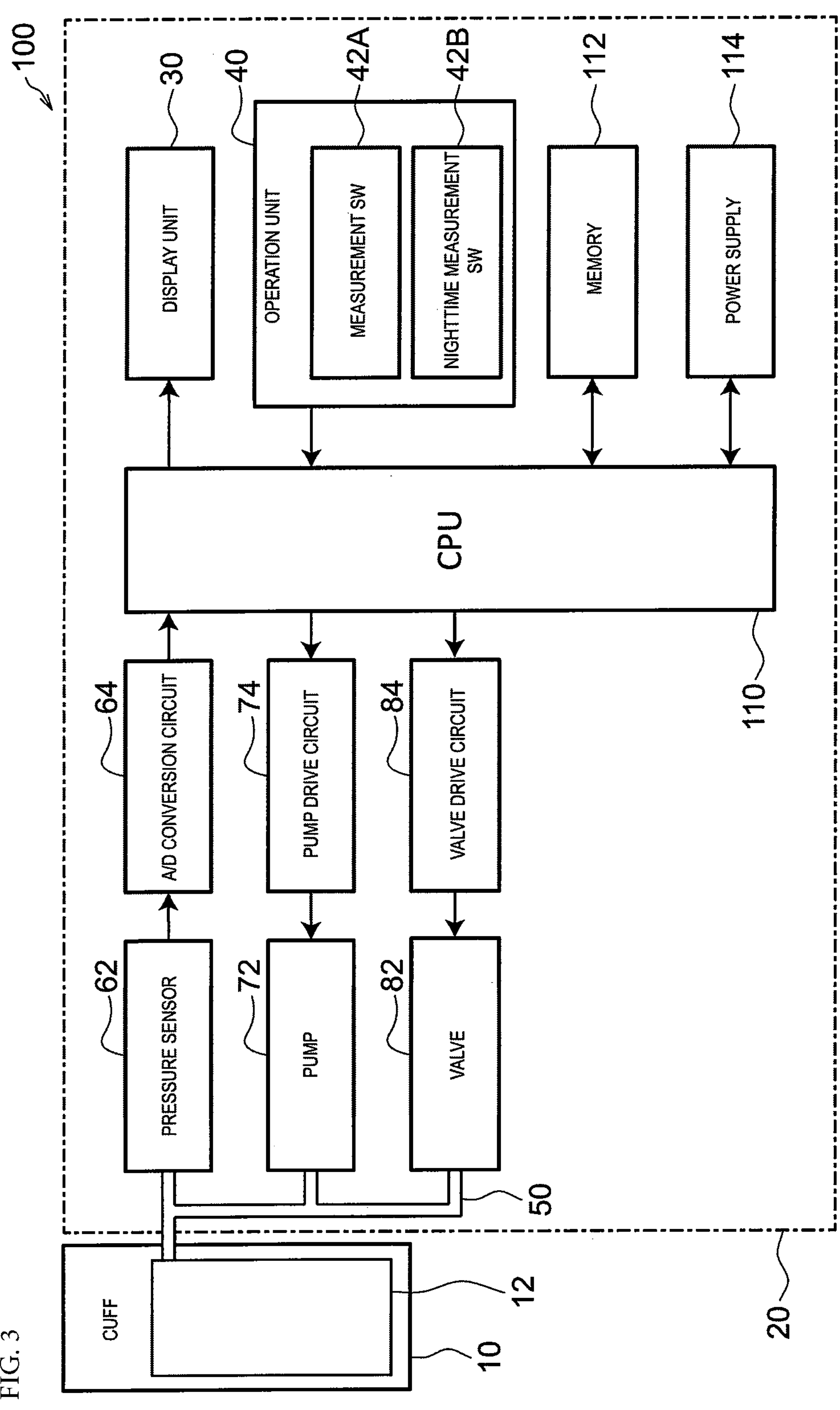
FIG. 3 is a block diagram of the wrist-type sphygmomanometer illustrated in FIG. 1.

FIG. 3 illustrates a block configuration of the sphygmomanometer 100.

The air bag 12 included in the cuff 10 described above and various fluid control devices (described below) included in the sphygmomanometer main body 20 are connected by an air pipe 50 in a manner that a fluid can circulate.

In addition to the display 30 and the operation unit 40 described above, the sphygmomanometer main body 20 includes a CPU 110 as a control unit, a memory 112 as an adjustment storage unit, a power supply unit 114, a pressure sensor 62, a pump 72, and a valve 82. Further, the sphygmomanometer main body 20 includes an A/D conversion circuit 64 that converts output of the pressure sensor 62 from an analog signal to a digital signal, a pump drive circuit 74 that drives the pump 72, and a valve drive circuit 84 that drives the valve 82. The pressure sensor 62, the pump 72, and the valve 82 are connected to the air bag 12 through the air pipe 50 in a manner that a fluid can circulate.

The memory 112 stores a program for controlling the sphygmomanometer 100, data used for controlling the sphygmomanometer 100, setting data for setting various functions of the sphygmomanometer 100, data of a measurement result of a blood pressure value, and the like. The memory 112 is also used as a work memory that temporarily stores various types of information during program execution. In particular, the memory 112 according to the embodiment is configured as a program storage unit, and stores a normal blood pressure measurement program and a nighttime blood pressure measurement program for calculating blood pressure by an oscillometric method, a measurement time setting program for setting a predetermined time (hereinafter, referred to as the absolute measurement time) and a time (hereinafter, referred to as the relative measurement time) provided at a predetermined time interval from a designated time, a measurement time comparison program for comparing the absolute measurement time and the relative measurement time, and a measurement time update program for updating the absolute measurement time or the relative measurement time, which will be described later.

The CPU (control unit) 110 is configured to control operation of the entire sphygmomanometer 100. Specifically, the CPU 110 is configured as a pressure control unit that drives the pump 72 or the valve 82 according to a program for controlling the sphygmomanometer 100 stored in the memory 112, a measurement time setting unit that executes a measurement time setting program to be described later, a measurement time comparison unit (determination unit) that executes a measurement time comparison program to be described later, a measurement time update unit (adjustment unit) that executes a measurement time update program to be described later, and a nighttime measurement implementation unit that executes the nighttime blood pressure measurement program at the absolute measurement time and the relative measurement time. The CPU 110 also displays, on the display 30, a blood pressure value obtained by executing the normal blood pressure measurement program or the nighttime blood pressure measurement program and the absolute measurement time and the relative measurement time of nighttime blood pressure measurement that are updated, and stores the blood pressure value and the updated absolute measurement time and relative measurement time in the memory 112.

In the embodiment, the power supply unit 114 includes a secondary battery, and is configured to supply power to each unit of the CPU 110, the pressure sensor 62, the pump 72, the valve 82, the display 30, the memory 112, the A/D conversion circuit 64, the pump drive circuit 74, and the valve drive circuit 84. The power supply unit 114 is also configured to be able to switch between on and off states, and becomes in the on state when the blood pressure measurement switch 42A is continuously pressed for three seconds or more, for example, in the off state.

The pump 72 is configured to supply air as a fluid to the air bag 12 through the air pipe 50 in order to increase the pressure (hereinafter, referred to as the "cuff pressure" as appropriate) in the air bag 12 built in the cuff 10. The valve 82 is configured to discharge air in the air bag 12 through the air pipe 50 by opening or hold cuff pressure by closing in order to control the cuff pressure. The pump drive circuit 74 is configured to drive the pump 72 based on a control signal provided from the CPU 110. The valve drive circuit 84 is configured to open and close the valve 82 based on a control signal provided from the CPU 110.

The pressure sensor 62 and the A/D conversion circuit 64 are configured to detect cuff pressure. The pressure sensor 62 in the embodiment is a piezoresistive pressure sensor, and detects and outputs the cuff pressure of the air bag 12 as electric resistance due to a piezoresistive effect. The A/D conversion circuit 64 converts output (electric resistance) of the pressure sensor 62 from an analog signal to a digital signal and outputs the digital signal to the CPU 110. In the embodiment, the CPU 110 acquires the cuff pressure according to the electric resistance output from the pressure sensor 62.

Blood Pressure Measurement Program

The blood pressure measurement program calculates blood pressure of the subject 200 with the sphygmomanometer main body 20 attached to the left wrist 210. The blood pressure measurement program includes a normal blood pressure measurement program and a nighttime blood pressure measurement program. The normal blood pressure measurement program assumes that the subject 200 sits on a chair or the like and keeps the left wrist 210 to which the sphygmomanometer main body 20 is attached at the same height as the heart of the subject 200. The nighttime blood pressure measurement program assumes that the subject 200 lies on a bed or the like, and the left wrist 210 to which the sphygmomanometer main body 20 is attached is placed at a position lower than the heart of the subject 200. It is known that different blood pressure values are calculated when a relationship between the height of the sphygmomanometer main body 20 and the height of the heart of the subject 200 is different. For this reason, in the normal blood pressure measurement program and the nighttime blood pressure measurement program, a parameter used for blood pressure calculation is adjusted in advance in consideration of a relationship between the height of the sphygmomanometer main body 20 and the height of the heart of the subject 200 assumed by the programs.

When performing the normal blood pressure measurement program or the nighttime blood pressure measurement program, the CPU 110 obtains a pulse wave signal from a fluctuation component of a pulse wave included in cuff pressure obtained by the pressure sensor 62, and calculates a blood pressure value (maximal blood pressure and minimal blood pressure) by using each program stored in the memory 112.

Nighttime Blood Pressure Measurement Mode

Figure 5A:
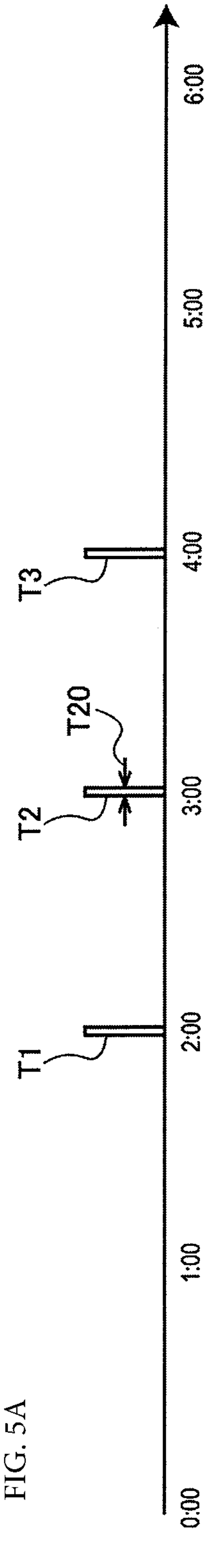
FIG. 5A is a schematic diagram illustrating adjustment of a measurement time by the wrist-type sphygmomanometer illustrated in FIG. 1.

The nighttime blood pressure measurement will be described. In the embodiment, 2:00 AM, 3:00 AM, and 4:00 AM are stored in advance in the memory 112 as initial values of the absolute measurement time at which the nighttime blood pressure measurement program is executed. The measurement time setting program refers to the above times stored in the memory 112 and sets them to absolute measurement times T1, T2, and T3 in the nighttime blood pressure measurement. FIG. 5A is a schedule of the absolute measurement times T1, T2, and T3, and illustrates that the nighttime blood pressure measurement program is executed for two minutes at the absolute measurement times T1, T2, and T3.

Figure 5B:
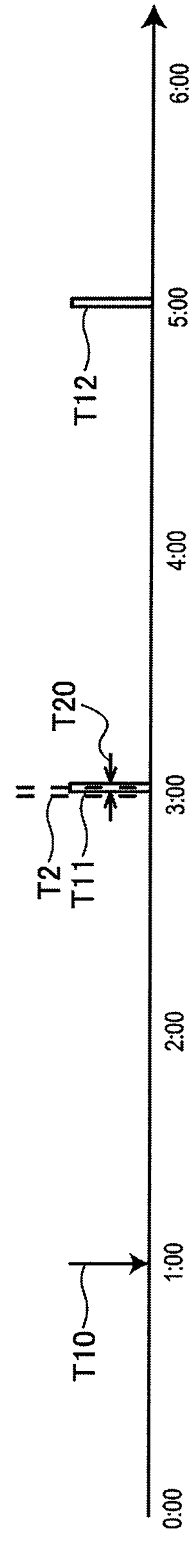
FIG. 5B is a schematic diagram illustrating adjustment of a measurement time by the wrist-type sphygmomanometer illustrated in FIG. 1.

When the subject 200 who has not slept yet presses the nighttime measurement switch 42B of the sphygmomanometer main body 20 once in a state where the cuff 10 of the sphygmomanometer 100 is wound around the left wrist 210 of the subject 200, a blood pressure measurement instruction (mode instruction) during the nighttime is output to the CPU 110. In this manner, the CPU 110 drives the pump 72 and the valve 82 to increase the cuff pressure of the cuff 10, and the left wrist 210 is temporarily pressed by the cuff 10. Further, a time at which the blood pressure measurement Instruction during nighttime is output to the CPU 110 is a designated time T10. The measurement time setting program sets times provided at two-hour intervals from the designated time T10 to relative measurement times T11 and T12. FIG. 5B is a schedule of the relative measurement times T11 and T12 when the designated time T10 is 1:01 AM, and indicates that the nighttime blood pressure measurement program is executed for two minutes at the relative measurement times T11 and T12 (in this case, the relative measurement time T11 is 3:01 AM, and the relative measurement time T12 is 5:01 AM).

The CPU 110 of the sphygmomanometer 100 compares the set absolute measurement times T1, T2, and T3 with the relative measurement times T11 and T12 based on the measurement time comparison program. In the embodiment, when determining that any of blood pressure measurement (first type schedule) performed at the absolute measurement times T1, T2, and T3 and any of blood pressure measurement (second type schedule) performed at the relative measurement times T11 and T12 overlap, the CPU 110 shifts the absolute measurement times T1, T2, and T3 or the relative measurement times T11 and T12 based on the measurement time update program.

After the above, the nighttime blood pressure measurement program is executed according to the schedule of the absolute measurement times T1, T2, and T3 and the schedule of the relative measurement times T11 and T12. However, when the nighttime measurement switch 42B is pushed down again during the time until the sphygmomanometer 100 performs blood pressure measurement of the subject 200 in sleep in the nighttime (for example, within waiting time until a time at which a predetermined nighttime blood pressure measurement program is executed), the nighttime blood pressure measurement is instructed to stop, and the nighttime blood pressure measurement program is not executed.

In the embodiment, the absolute measurement times T1, T2, and T3 are set to 2:00 AM, 3:00 AM, and 4:00 AM, respectively. However, the present invention is not limited to this content, and the absolute measurement times T1, T2, and T3 may be set to different times such as 0:00 AM and 1:00 AM, for example. Further, the relative measurement times T11 and T12 are set to times provided at two-hour intervals from the designated time T10. However, the present invention is not limited to this content, and the relative measurement times T11 and T12 may be set to, for example, times one hour and three hours after the designated time T10.

Figure 4:
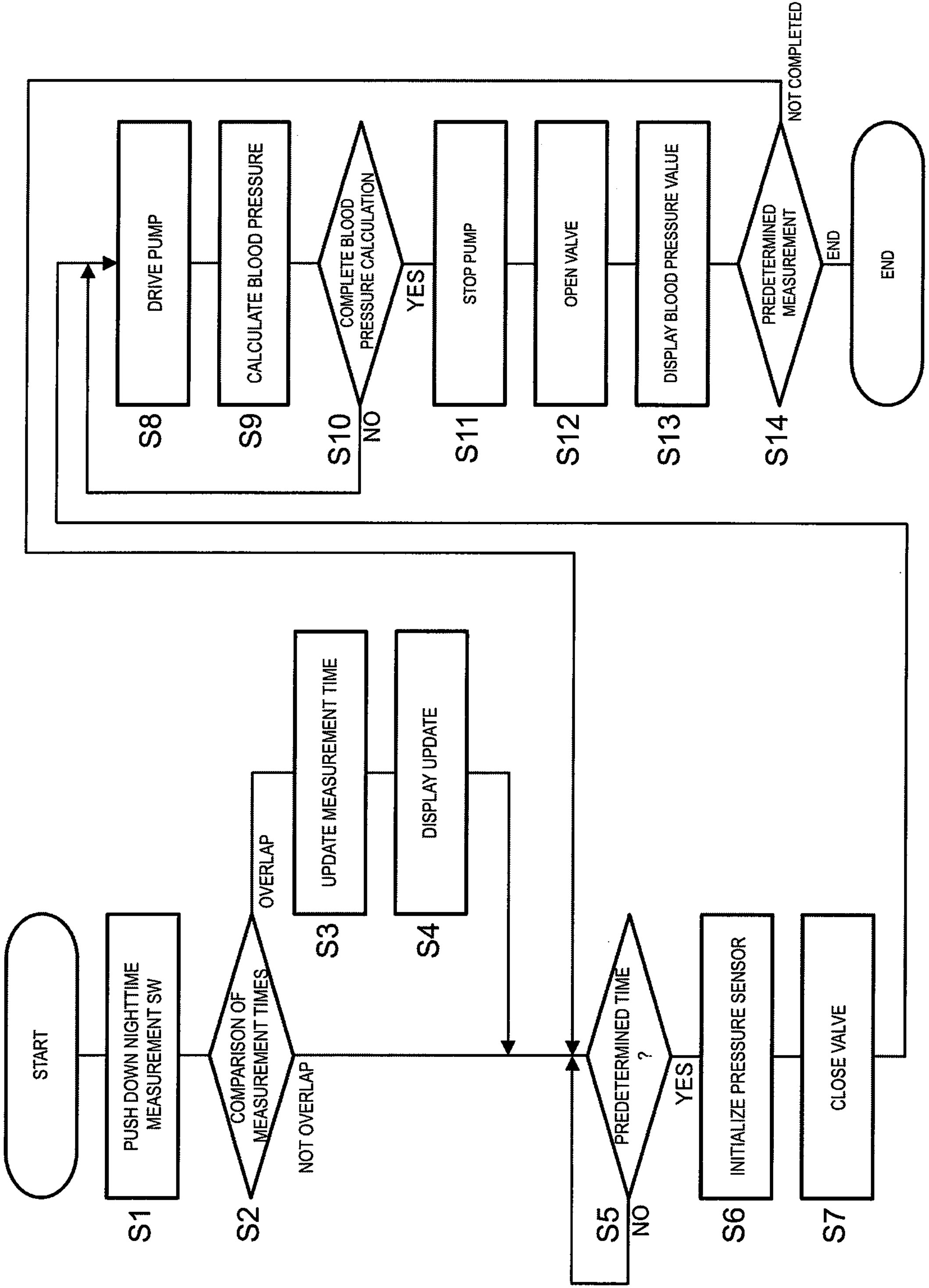
FIG. 4 is a flowchart of nighttime blood pressure measurement performed by the wrist-type sphygmomanometer illustrated in FIG. 1.

FIG. 4 illustrates an operation process when the subject 200 performs the nighttime blood pressure measurement by the sphygmomanometer 100. During the nighttime blood pressure measurement, the subject 200 wearing the sphygmomanometer 100 on the left wrist 210 remains to be in a state of lying on a bed or the like. Further, when the power supply unit 114 is in an on state, the absolute measurement times T1, T2, and T3 are already set.

In this state, as shown in Step S1 of FIG. 4, when the subject 200 presses the nighttime measurement switch 42B provided on the sphygmomanometer main body 20 and inputs a nighttime blood pressure measurement instruction, the CPU 110 sets the above-described relative measurement times T11 and T12 based on the designated time T10 by the measurement time setting program.

Next, based on the measurement time comparison program, the CPU 110 determines whether or not the blood pressure measurement performed at the set absolute measurement times T1, T2, and T3 and the blood pressure measurement performed at the relative measurement times T11 and T12 overlap (Step S2). Specifically, the measurement time comparison program sets a length of a time zone of measurement (time zone of the first blood pressure measurement) at the absolute measurement times T1, T2, and T3 and a length of a time zone of measurement (time zone of the second blood pressure measurement) at the relative measurement times T11 and T12 to required measurement time T20 (two minutes in the embodiment) of a certain length required for measurement. In this manner, the length of the time zone of measurement at the absolute measurement times T1, T2, and T3 and the length of the time zone of measurement at the relative measurement times T11 and T12 are easily set. When the time zone of measurement at the absolute measurement times T1, T2, and T3 and the time zone of measurement at the relative measurement times T11 and T12 at least partially overlap, it is determined that the blood pressure measurement performed at the absolute measurement times T1, T2, and T3 and the blood pressure measurement performed at the relative measurement times T11 and T12 "overlap" (have an affirmative result). In contrast, when the time zone of measurement at the absolute measurement times T1, T2, and T3 and the time zone of measurement at the relative measurement times T11 and T12 do not overlap at all, it is determined that the blood pressure measurement performed at the absolute measurement times T1, T2, and T3 and the blood pressure measurement performed at the relative measurement times T11 and T12 "do not overlap".

As illustrated in FIGS. 5A and 5B, the absolute measurement times T1, T2, and T3 are set to 2:00 AM, 3:00 AM, and 4:00 AM, respectively, and the relative measurement times T11 and T12 are set to 3:01 AM and 5:01 AM, respectively. At this time, an absolute measurement time zone of the absolute measurement time T2 (3:00 AM) and a relative measurement time zone of the relative measurement time T11 (3:01 AM) partially overlap (the relative measurement time T11 is within the absolute measurement time zone of the absolute measurement time T2). Therefore, the blood pressure measurement performed at the absolute measurement time T2 and the blood pressure measurement performed at the relative measurement time T11 are determined to "overlap". In contrast, since the other absolute measurement time zones and the relative measurement time zone do not overlap at all (the relative measurement time T12 is not within absolute measurement time zones of the other absolute measurement times), the blood pressure measurement performed at the other absolute measurement times and the relative measurement time is determined "not to overlap". In this manner, a length of the time zone of measurement at the absolute measurement times T1, T2, and T3 and a length of the time zone of measurement at the relative measurement times T11 and T12, which are used for determination, become constant, so that a stable determination result can be obtained.

When the blood pressure measurement performed at the absolute measurement times T1, T2, and T3 and the blood pressure measurement performed at the relative measurement times T11 and T12 are determined to "overlap" in Step S2, the CPU 110 adjusts the absolute measurement times T1, T2, and T3 and the relative measurement times T11 and T12 based on the measurement time update program (Step S3). Specifically, the measurement time update program shifts the relative measurement times T11 and T12 such that idle time T22 of a certain length, for example, one minute is provided between the absolute measurement time zones of the absolute measurement times T1, T2, and T3 and the relative measurement time zones of the relative measurement times T11 and T12. In this manner, a length of the idle time T22 may be easily set.

Figure 5C:
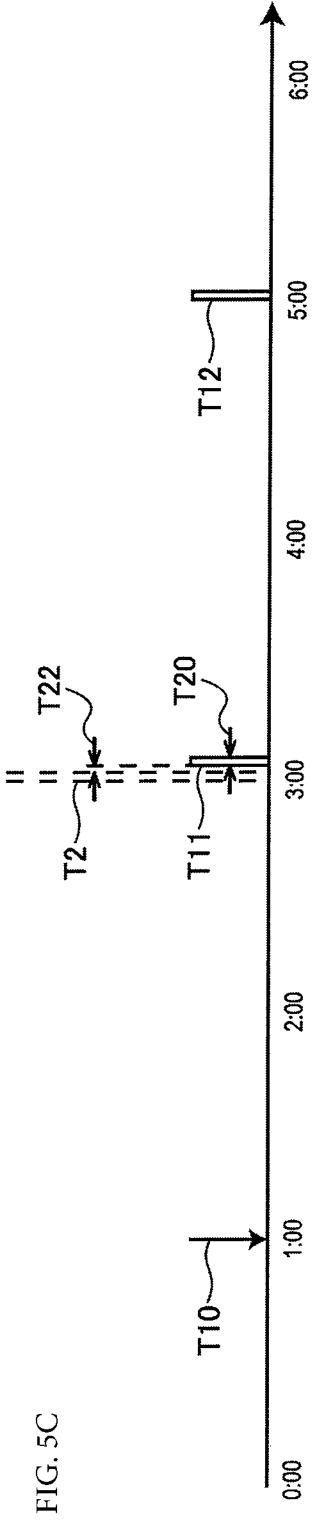
FIG. 5C is a schematic diagram illustrating adjustment of a measurement time by the wrist-type sphygmomanometer illustrated in FIG. 1.

As illustrated in FIGS. 5A and 5B, since an absolute measurement time zone of the absolute measurement time T2 and a relative measurement time zone of the relative measurement time T11 partially overlap with each other among the absolute measurement times T1, T2, and T3 and the relative measurement times T11 and T12 that are set first, the blood pressure measurement performed at the absolute measurement time T2 and the blood pressure measurement performed at the relative measurement time T11 are determined to "overlap". At this time, based on the measurement time update program, the CPU 110 delays the relative measurement time T11, that is, updates the relative measurement time T11 from 3:01 AM to 3:03 AM (see FIG. 5C) so as to provide the idle time T22 between the absolute measurement time zones of the absolute measurement times T1, T2, and T3 and the relative measurement time zones of the relative measurement times T11 and T12, that is, to extend time from a scheduled end time (3:02 AM) of the measurement at the absolute measurement time T2 to a scheduled start time (3:01 AM) of the measurement at the relative measurement time T11 to the idle time T22 (one minute). Therefore, the blood pressure measurement performed at the absolute measurement time T2 and the blood pressure measurement performed at the relative measurement time T11 are set "not to overlap". In this manner, after the subject 200 inputs a nighttime blood pressure measurement instruction by the nighttime measurement switch 42B, adjustment by the CPU 110 is performed within time in which the subject 200 is expected not to have fallen asleep yet. Further, a situation in which the blood pressure measurement is continuously performed is avoided, and physical burden on the subject 200 is reduced.

At this time, the CPU 110 stores that the absolute measurement times T1, T2, and T3 and the relative measurement times T11 and T12 are adjusted in the memory 112 together with the absolute measurement times T1, T2, and T3 and the adjusted relative measurement times T11 and T12. In this manner, when the blood pressure measurement (blood pressure measurement performed at the absolute measurement times T1, T2, and T3) performed at a predetermined time and the blood pressure measurement (blood pressure measurement performed at the relative measurement times T11 and T12) performed at a predetermined time interval from going to sleep overlap or are close to each other in the nighttime blood pressure measurement, the subject 200 can confirm that a situation in which the blood pressure measurement is continuously performed is avoided afterwards, for example, after getting up.

After the above, the CPU 110 outputs the absolute measurement times T1, T2, and T3 and the adjusted relative measurement times T11 and T12 to the display 30 to indicate that the relative measurement times T11 and T12 are updated (Step S4). In this manner, the subject 200 views the display of the display 30 and can recognize that the blood pressure measurement performed at the absolute measurement times T1, T2, and T3 and the blood pressure measurement performed at the relative measurement times T11 and T12 are determined to "overlap" (a determination result is an affirmative result), and that adjustment processing of adjusting the relative measurement times T11 and T12 is performed.

After the above, the CPU 110 determines whether it is the absolute measurement times T1, T2, and T3 or the relative measurement times T11 and T12 (Step S5), and if it is not any of the measurement times (when the process proceeds to NO in Step S5), it waits until the measurement time comes.

When it is the measurement time (when the process proceeds to YES in Step S5), the CPU 110 initializes the pressure sensor 62 (Step S6). Specifically, the CPU 110 initializes a processing memory area, stops the pump 72, and performs 0 mmHg adjustment (setting the atmospheric pressure to 0 mmHg) of the pressure sensor 62 in a state where the valve 82 is opened.

Next, the CPU 110 closes the valve 82 via the valve drive circuit 84 (Step S7), and then drives the pump 72 via the pump drive circuit 74 to start pressurization of the cuff 10 (air bag 12) (Step S8). At this time, the CPU 110 controls a pressurization rate of cuff pressure, which is pressure in the air bag 12, based on output of the pressure sensor 62 while supplying air from the pump 72 to the air bag 12 through the air pipe 50.

Next, in Step S9, the CPU 110 calculates a blood pressure value (maximal blood pressure and minimal blood pressure) by using the above-described nighttime blood pressure measurement program stored in the memory 112 based on a pulse wave signal acquired at this time point.

At this time point, when the blood pressure value cannot be calculated yet due to insufficient data (when the process proceeds to NO in Step S10), the CPU 110 repeats the processing of Steps S8 and S9 unless the cuff pressure reaches an upper limit pressure (which is predetermined for safety at, for example, 300 mmHg).

When the blood pressure value is calculated (in a case where the process proceeds to YES in Step S10), the CPU 110 performs control to stop the pump 72 (Step S11), open the valve 82 (Step S12), and exhaust the air in the cuff 10 (air bag 12).

After the above, the CPU 110 displays the calculated blood pressure value on the display 30 (Step S13), and performs control to store the blood pressure value in the memory 112.

When one time of blood pressure measurement set in the schedule described above is completed, the CPU 110 determines whether or not all the blood pressure measurements set in the above schedule are completed (Step S14). In a case where the blood pressure measurement set in the schedule described above is still scheduled (when the process proceeds to "not completed" in Step S14), the CPU 110 returns to Step S5, determines whether or not it is a next measurement time among the absolute measurement times T1, T2, and T3 and the relative measurement times T11 and T12, and waits until the measurement time comes if it is not the measurement time (when the process proceeds to NO in Step S5).

When it is a next measurement time among the absolute measurement times T1, T2, and T3 and the relative measurement times T11 and T12 (when the process proceeds to YES in Step S5), the CPU 110 repeats the processing of Steps S6 to S13, and again determines whether or not all the blood pressure measurements at the absolute measurement times T1, T2, and T3 and the relative measurement times T11 and T12 are completed in Step S14.

When all the blood pressure measurements at the absolute measurement times T1, T2, and T3 and the relative measurement times T11 and T12 are completed (when the process proceeds to "end" in Step S14), the CPU 110 ends the nighttime blood pressure measurement.

Figure 6:
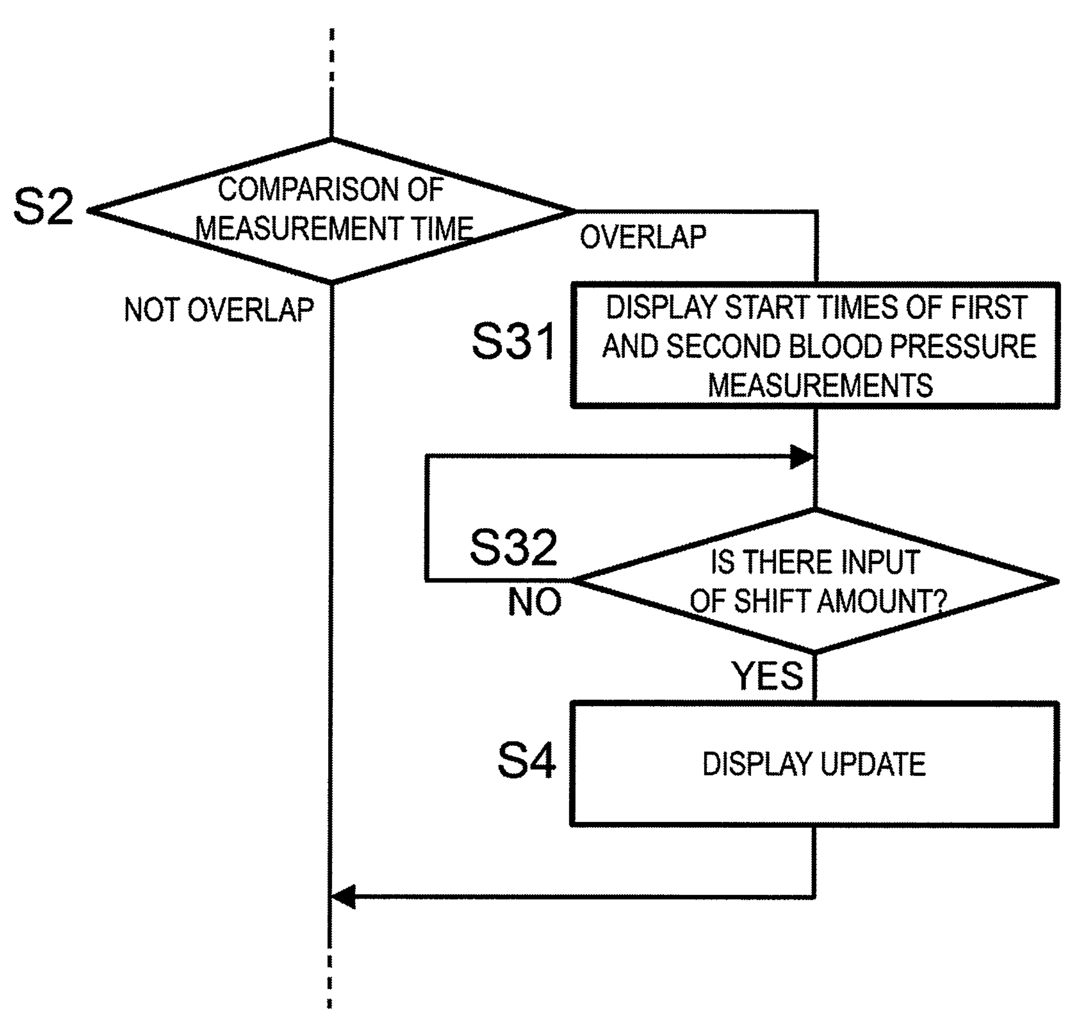
FIG. 6 is a flowchart for shifting a measurement time by the wrist-type sphygmomanometer illustrated in FIG. 1.

Note that, in the measurement time update program described above, the relative measurement times T11 and T12 are shifted so that the idle time T22 of a certain length (in the above example, one minute) is provided between the absolute measurement time zones of the absolute measurement times T1, T2, and T3 and the relative measurement time zones of the relative measurement times T11 and T12. However, the present invention is not limited to this. For example, the idle time may be provided as desired by the user. Specifically, when a time zone of measurement at the absolute measurement times T1, T2, and T3 and a time zone of measurement at the relative measurement times T11 and T12 at least partially overlap (Step S2 in FIG. 4), as shown in Step S31 in FIG. 6, the CPU 110 causes the display 30 to display the absolute measurement times T1, T2, and T3 as start times of the first blood pressure measurement and the relative measurement times T11 and T12 as start times of the second blood pressure measurement. Next, the CPU 110 determines whether or not the subject 200 inputs a shift amount by which to shift a start time of the blood pressure measurement by operating the nighttime measurement switch (time operation unit) 42B in order to adjust the relative measurement times T11 and T12 (Step S32). If the subject 200 does not input the shift amount (when the process proceeds to NO in Step S32), the CPU 110 waits until the subject 200 inputs the shift amount. In contrast, when the subject 200 operates the nighttime measurement switch 42B to input the shift amount (when the process proceeds to YES in Step S32), the CPU 110 shifts one of the absolute measurement times T1, T2, and T3 and the relative measurement times T11 and T12 by using the input shift amount to provide idle time (T22') between the absolute measurement times T1, T2, and T3 and the relative measurement times T11 and T12. For example, in the example of overlap of FIGS. 5A and 5B, the relative measurement time T11 is shifted in a direction of being delayed by the input shift amount (for example, three minutes), and the idle time T22' is provided between the absolute measurement time T2 and the relative measurement time T11. In this manner, the idle time T22' can be provided between the absolute measurement time zones of the absolute measurement times T1, T2, and T3 and the relative measurement time zones of the relative measurement times T11 and T12 as desired by the subject 200.

Figure 7A:
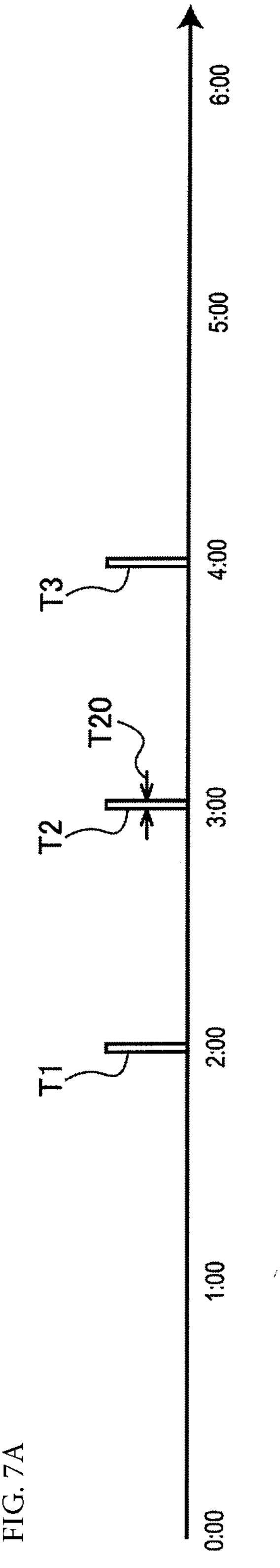
FIG. 7A is a schematic diagram illustrating adjustment of a measurement time by the wrist-type sphygmomanometer of another embodiment.
Figure 7B:
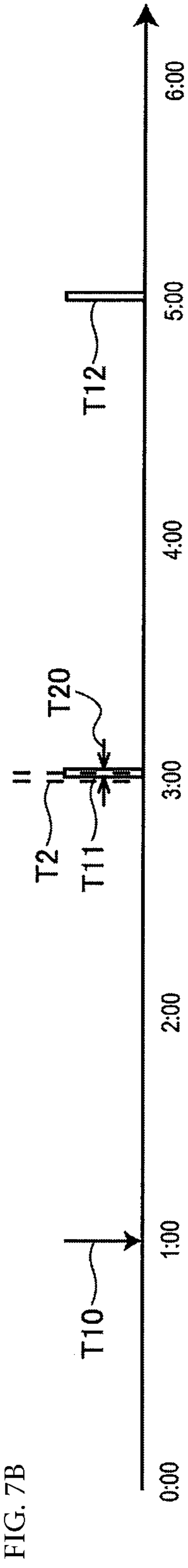
FIG. 7B is a schematic diagram illustrating adjustment of a measurement time by the wrist-type sphygmomanometer of another embodiment.
Figure 7C:
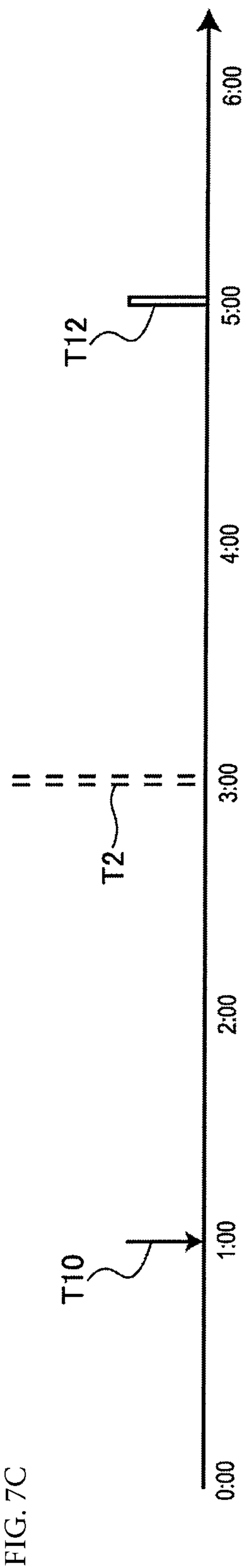
FIG. 7C is a schematic diagram illustrating adjustment of a measurement time by the wrist-type sphygmomanometer of another embodiment.

Further, in the measurement time update program described above, the relative measurement times T11 and T12 are shifted so that the idle time T22 is provided between the absolute measurement time zones of the absolute measurement times T1, T2, and T3 and the relative measurement time zones of the relative measurement times T11 and T12. In this manner, the blood pressure measurement performed at the absolute measurement times T1, T2, and T3 and the blood pressure measurement performed at the relative measurement times T11 and T12 are adjusted so as not to overlap with each other. In contrast, as illustrated in FIGS. 7A to 7C, when the absolute measurement time zone of the absolute measurement time T2 and the relative measurement time zone of the relative measurement time T11 partially overlap with each other among the absolute measurement times T1, T2, and T3 and the relative measurement times T11 and T12 that are set first, the measurement time update program may perform adjustment such that the blood pressure measurement performed at the absolute measurement time T2 and the blood pressure measurement performed at the relative measurement time T11 do not overlap by disabling the blood pressure measurement at the relative measurement time T11.

When the time zone of measurement at the absolute measurement times T1, T2, and T3 and the time zone of measurement at the relative measurement times T11 and T12 at least partially overlap, the measurement time comparison program determines that the blood pressure measurement performed at the absolute measurement times T1, T2, and T3 and the blood pressure measurement performed at the relative measurement times T11 and T12 "overlap". In contrast, also in a case where a time difference between the time zone of measurement at the absolute measurement times T1, T2, and T3 and the time zone of measurement at the relative measurement times T11 and T12 is equal to or less than a predetermined value, for example, one minute or less, the blood pressure measurement performed at the absolute measurement times T1, T2, and T3 and the blood pressure measurement performed at the relative measurement times T11 and T12 may be determined to "overlap". In this manner, the CPU 110 can reliably provide one minute, which is predetermined extended time, between the absolute measurement time zones of the absolute measurement times T1, T2, and T3 and the relative measurement time zones of the relative measurement times T11 and T12.

When the blood pressure measurement (blood pressure measurement performed at the absolute measurement times T1, T2, and T3) performed at a predetermined time and the blood pressure measurement (blood pressure measurement performed at the relative measurement times T11 and T12) performed at a predetermined time interval from going to sleep overlap or are close to each other in the nighttime blood pressure measurement, a situation in which the blood pressure measurement is continuously performed is avoided. Therefore, the physical burden on the subject 200 is small, and sleep is not inhibited.

Since the sphygmomanometer 100 is of a type that presses a wrist (the left wrist 210 in the embodiment, which may be the right wrist) as a measured site, it is expected that the sphygmomanometer 100 is less likely to disturb sleep of the subject 200 than that of a type that presses an upper arm. Therefore, the sphygmomanometer 100 is suitable for the nighttime blood pressure measurement.

Further, since the sphygmomanometer 100 is integrally and compactly configured as a wrist-type sphygmomanometer, the subject 200 can easily handle the sphygmomanometer.

Other Embodiments

Figure 8:
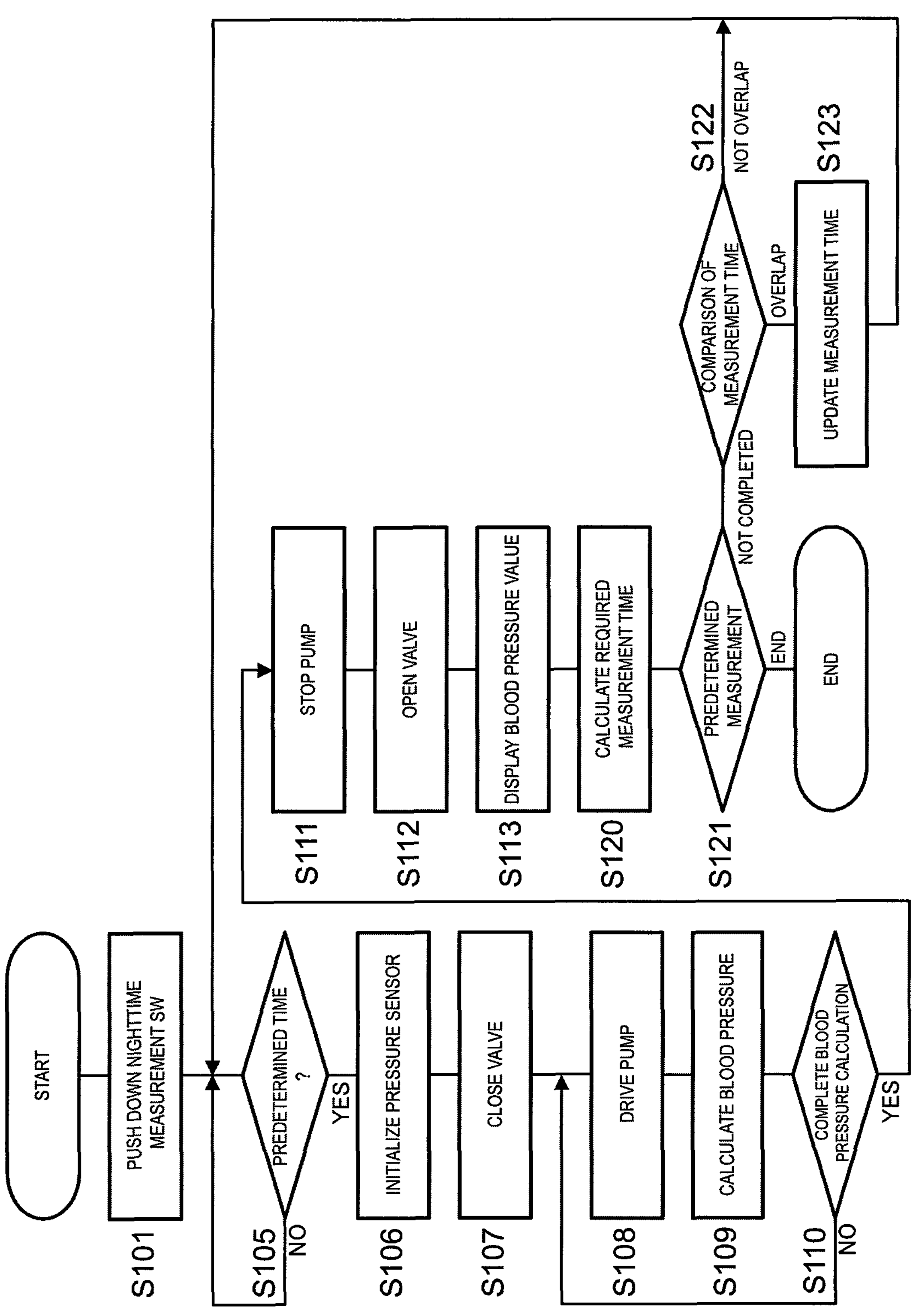
FIG. 8 is a flowchart of nighttime blood pressure measurement performed by the wrist-type sphygmomanometer of another embodiment.

In the above-described embodiment, the measurement time comparison program (Step S2) and the measurement time update program (Step S3) are executed before the absolute measurement times T1, T2, and T3 and the relative measurement times T11 and T12, but may be executed after the blood pressure measurement at the absolute measurement times T1, T2, and T3 and the relative measurement times T11 and T12 is completed as illustrated in FIG. 8. In this case, the CPU 110 preferably calculates time required for the measurement (Step S120) after a calculated blood pressure value is displayed (Step S113). The CPU 110 may store the calculated time in the memory (time storage unit) 112 as the required measurement time T20. Further, the required measurement time T20 stored in the memory 112 is not limited to time required for the blood pressure measurement at the absolute measurement times T1, T2, and T3 and the relative measurement times T11 and T12, and may be, for example, time required when measurement is performed in the normal blood pressure measurement mode before the sphygmomanometer 100 is set to the nighttime blood pressure measurement mode. After the above, if not all the blood pressure measurements at the absolute measurement times T1, T2, and T3 and the relative measurement times T11 and T12 are completed (when the process proceeds to "not completed" in Step S121), the CPU 110 executes the measurement time comparison program (Step S122). In this manner, since the CPU 110 makes a determination based on actual required measurement time, the accuracy of setting a length of the time zone is improved, and an appropriate determination result can be obtained. When the blood pressure measurement performed at a next one of the absolute measurement times T1, T2, and T3 and the blood pressure measurement performed at a next one of the relative measurement times T11 and T12 are determined to "overlap", the CPU 110 adjusts the next one of the absolute measurement times T1, T2, and T3 and the next one of the relative measurement times T11 and T12 based on the measurement time update program (Step S123). After the adjustment of the next one of the absolute measurement times T1, T2, and T3 and the next one of the relative measurement times T11 and T12 is completed, or when the blood pressure measurement performed at the next one of the absolute measurement times T1, T2, and T3 and the blood pressure measurement performed at the next one of the relative measurement times T11 and T12 are determined "not to overlap", the CPU 110 returns to Step S105 of determining whether or not the absolute measurement times T1, T2, and T3 or the relative measurement times T11 and T12 come. In this manner, the adjustment by the CPU 110 is performed every time the blood pressure measurement performed at the absolute measurement times T1, T2, and T3 or the blood pressure measurement performed at the relative measurement times T11 and T12 is performed. Other steps are performed similarly to those in the operation process illustrated in FIG. 4.

In the above-described embodiment, the measurement time update program adjusts the relative measurement times T11 and T12, but may be configured to adjust the absolute measurement times T1, T2, and T3.

In the above-described embodiment, the CPU 110 calculates blood pressure in a pressurization process of the cuff 10 (air bag 12), but may calculate the blood pressure in a depressurization process of the cuff.

In the above-described embodiment, the sphygmomanometer 100 includes the blood pressure measurement switch 42A to which a normal blood pressure measurement instruction is input and the nighttime measurement switch 42B to which a nighttime blood pressure measurement instruction is input. However, for example, a signal receiving unit of the sphygmomanometer receives the instruction (mode instruction) from a smartphone or the like existing outside the sphygmomanometer via wireless communication, and the signal received by the signal receiving unit may be replaced with a signal output from the normal blood pressure measurement switch or the nighttime measurement switch to the CPU.

In the above-described embodiment, the sphygmomanometer 100 is configured such that the blood pressure measurement switch 42A outputs a signal of the normal blood pressure measurement instruction to the CPU 110, and the nighttime measurement switch 42B outputs a signal of the nighttime blood pressure measurement instruction to the CPU 110. However, for example, the configuration may be such that the blood pressure measurement switch is pressed once to output the signal (mode instruction) of the normal blood pressure measurement instruction to the CPU, and the blood pressure measurement switch is pressed twice within a certain time to output the signal (mode instruction) of the nighttime blood pressure measurement instruction to the CPU.

In the above-described embodiment, the sphygmomanometer main body 20 is integrally attached to the cuff 10, but may be provided separately from the cuff and connected to the cuff 10 (air bag 12) via a flexible air tube in a manner that a fluid can circulate.

In the above-described embodiment, the normal blood pressure measurement program, the nighttime blood pressure measurement program, the measurement time setting program, the measurement time comparison program, the measurement time update program, and a process of these are stored in the memory 112 as software, but may be recorded on a non-transitory medium such as a compact disk (CD), a digital universal disk (DVD), a flash memory, or the like. By installing software recorded in the above-described medium in a substantial computer device such as a personal computer, a personal digital assistant (PDA), or a smartphone, the above-described programs and process can be executed by the computer device.

As described above, a sphygmomanometer of the present disclosure has a nighttime blood pressure measurement mode for automatically starting blood pressure measurement according to a predetermined schedule, wherein the schedule includes a first type schedule in which blood pressure measurement is started at a predetermined time and a second type schedule in which blood pressure measurement is started at a predetermined time interval from a designated time, the sphygmomanometer comprising:

a control unit that disables one of first blood pressure measurement scheduled based on the first type schedule and second blood pressure measurement scheduled based on the second type schedule or changes one of a start time of the first blood pressure measurement and a start time of the second blood pressure measurement to provide idle time between the first blood pressure measurement and the second blood pressure measurement in a case where a time zone of the first blood pressure measurement and a time zone of the second blood pressure measurement at least partially overlap with each other or in a case where a time difference between the time zone of the first blood pressure measurement and the time zone of the second blood pressure measurement is equal to or less than a predetermined value.

In the present description, the “first type schedule” and the “second type schedule” included in the “schedule” define start times of blood pressure measurement (which usually requires for about one minute to two minutes). The “time interval” of the blood pressure measurement in the “second type schedule” means an interval between the “designated time” and a start time of certain blood pressure measurement or an interval between a start time of certain blood pressure measurement and a next start time, and is assumed to have the same meaning as a cycle.

The “designated time” means a time designated by the user (typically, the subject) of the sphygmomanometer, and may be, for example, a time when the user inputs an instruction to make a transition to the nighttime blood pressure measurement mode to the sphygmomanometer.

The “time zone” of the blood pressure measurement refers to time (for example, in the oscillometric method in which a measured site of the subject is temporarily pressed by a blood pressure measuring cuff to measure blood pressure, it usually takes about one minute to two minutes) in which the blood pressure measurement is actually performed.

According to this sphygmomanometer, in a case where the time zone of the first blood pressure measurement and the time zone of the second blood pressure measurement at least partially overlap, or in a case where the time difference between the time zone of the first blood pressure measurement and the time zone of the second blood pressure measurement is equal to or less than a predetermined value (small), the control unit adjusts the scheduled start time of the first blood pressure measurement or the scheduled start time of the second blood pressure measurement. That is, the control unit disables one of the first blood pressure measurement and the second blood pressure measurement, or changes one of the start time of the first blood pressure measurement and the start time of the second blood pressure measurement to provide the idle time between the first blood pressure measurement and the second blood pressure measurement. In this manner, in the nighttime blood pressure measurement, when the blood pressure measurement performed at the predetermined time overlaps with or is close to the blood pressure measurement performed at the predetermined time interval from going to sleep, a situation in which the blood pressure measurement is continuously performed is avoided. Therefore, the physical burden on the subject is small, and sleep is not inhibited.

The present disclosure provides the sphygmomanometer according to one embodiment, further comprising:

a mode operation unit that inputs a mode instruction for switching a mode to the nighttime blood pressure measurement mode, wherein the control unit includes:

a first determination unit that determines whether or not the time zone of the first blood pressure measurement scheduled based on the first type schedule and the time zone of the second blood pressure measurement scheduled based on the second type schedule at least partially overlap with each other or whether or not the time difference between the time zone of the first blood pressure measurement and the time zone of the second blood pressure measurement is equal to or less than the predetermined value as the mode instruction is input and transition is made to the nighttime blood pressure measurement mode; and a first adjustment unit that performs adjustment to disable one of the first blood pressure measurement and the second blood pressure measurement or provide the idle time between the first blood pressure measurement and the second blood pressure measurement by changing one of the start time of the first blood pressure measurement and the start time of the second blood pressure measurement as a result of the determination is obtained in a case where the result of the determination is an affirmative result that the time zones partially overlap or the time difference is equal to or less than the predetermined value.

“Transition is made to the nighttime blood pressure measurement mode” typically refers to a time point at which transition is made to the nighttime blood pressure measurement mode, but may be within time in which the subject is expected not to fall asleep yet, for example, within five minutes from the time point. Similarly, “as a result of the determination is obtained” typically refers to a time point at which a result of the determination is obtained, but may be within time in which the subject is expected not to fall asleep yet, for example, within five minutes from the time point.

According to the sphygmomanometer, a result of the determination is obtained as the mode instruction is input and the sphygmomanometer makes a transition to the nighttime blood pressure measurement mode, and the adjustment by the first adjustment unit is performed as an affirmative result of the determination is obtained. Therefore, after the subject inputs the mode instruction by the mode operation unit, the adjustment by the first adjustment unit is performed within time in which the subject is expected to have not fallen asleep yet.

The present disclosure provides the sphygmomanometer according to one embodiment, further comprising:

a display; and a time operation unit for inputting a shift amount by which to shift a start time of blood pressure measurement, wherein the first adjustment unit displays the start time of the first blood pressure measurement and/or the start time of the second blood pressure measurement on the display in the case where the result of the determination is the affirmative result, and provides the idle time between the first blood pressure measurement and the second blood pressure measurement by shifting one of the start time of the first blood pressure measurement and the start time of the second blood pressure measurement by using the shift amount input by the time operation unit.

"To shift a start time" of the blood pressure measurement refers to moving the start time in an advancing direction or a delaying direction.

According to this sphygmomanometer, in a case where the result of the determination is the affirmative result, the first adjustment unit causes the display to display the start time of the first blood pressure measurement and/or the start time of the second blood pressure measurement. Therefore, the user (primarily, the subject) can recognize that the result of the determination is the affirmative result and adjustment processing is necessary by viewing display on the display. Here, when the user inputs the shift amount by which to shift the start time of the blood pressure measurement by the time operation unit, the first adjustment unit shifts one of the start time of the first blood pressure measurement and the start time of the second blood pressure measurement by using the shift amount input by the time operation unit to provide the idle time between the first blood pressure measurement and the second blood pressure measurement. For example, the start time of the second blood pressure measurement is shifted in a direction to be delayed by the shift amount input by the time operation unit. In this manner, the idle time can be provided between the first blood pressure measurement and the second blood pressure measurement as desired by the user.

The present disclosure provides the sphygmomanometer according to one embodiment, wherein the control unit includes:

a second determination unit that determines whether or not a time zone of next first blood pressure measurement scheduled based on the first type schedule and a time zone of next second blood pressure measurement scheduled based on the second type schedule at least partially overlap with each other or whether or not a time difference between the time zone of the next first blood pressure measurement and the time zone of the next second blood pressure measurement is equal to or less than the predetermined value as the first blood pressure measurement based on the first type schedule or the second blood pressure measurement based on the second type schedule is performed in the nighttime blood pressure measurement mode; and a second adjustment unit that performs adjustment to disable one of the next first blood pressure measurement and the next second blood pressure measurement or provide the idle time between the next first blood pressure measurement and the next second blood pressure measurement by changing one of a start time of the next first blood pressure measurement and a start time of the next second blood pressure measurement as a result of the determination is obtained in a case where the result of the determination is an affirmative result that the time zones partially overlap or the time difference is equal to or less than the value.

"As the first blood pressure measurement based on the first type schedule or the second blood pressure measurement based on the second type schedule is performed" typically refers to a time point immediately after the first blood pressure measurement or the second blood pressure measurement is performed, but may be within time until next blood pressure measurement is performed, for example, within five minutes from the time point. Similarly, "as a result of the determination is obtained" typically refers to a time point at which a result of the determination is obtained, but may be within time until next blood pressure measurement is performed, for example, within five minutes from the time point.

According to the sphygmomanometer, a result of the determination is obtained as the first blood pressure measurement or the second blood pressure measurement is performed, and the adjustment by the second adjustment unit is performed as an affirmative result of the determination is obtained. Therefore, each time the first blood pressure measurement or the second blood pressure measurement is performed, the adjustment by the second adjustment unit is performed.

The present disclosure provides the sphygmomanometer according to one embodiment, further comprising:

a time storage unit that stores required measurement time actually required for past blood pressure measurement, wherein the control unit sets a length of a time zone of the first blood pressure measurement and a length of a time zone of the second blood pressure measurement based on at least required measurement time required for previous blood pressure measurement.

Here, "length of a time zone" means a length of time for setting a time zone.

According to this sphygmomanometer, the required measurement time actually required for past blood pressure measurement is stored in the time storage unit. The control unit sets a length of the time zone of the first blood pressure measurement and a length of the time zone of the second blood pressure measurement based on at least required measurement time required for previous blood pressure measurement. Therefore, the accuracy of setting a length of the time zone is improved, and an appropriate determination result can be obtained.

The present disclosure provides the sphygmomanometer according to one embodiment, wherein the control unit sets a length of a time zone of the first blood pressure measurement and a length of a time zone of the second blood pressure measurement to a certain length.

Here, "certain length" refers to a length that is not unnecessarily long for next blood pressure measurement after normal blood pressure measurement is completed, for example, two minutes.

According to the sphygmomanometer the control unit sets a length of a time zone of the first blood pressure measurement and a length of a time zone of the second blood pressure measurement to a certain length. Therefore, the length of the time zone may be easily set. Further, since the length of the time zone is set to a certain length, a stable determination result can be obtained.

The present disclosure provides the sphygmomanometer according to one embodiment, wherein the control unit sets the idle time to a certain length.

Here, "certain length" refers to time (for example, in the oscillometric method in which a measured site of the subject is temporarily pressed by a blood pressure measuring cuff to measure blood pressure, it usually takes about one minute) that is preferably provided between measurements in consideration of physical burden on the subject.

According to this sphygmomanometer, the control unit sets the idle time to a certain length. Therefore, the length of the idle time may be easily set. Further, a situation in which the blood pressure measurement is continuously performed is avoided, and physical burden on the subject is reduced.

The present disclosure provides the sphygmomanometer according to one embodiment, further comprising:

an adjustment storage unit that stores that the control unit disables one of the first blood pressure measurement and the second blood pressure measurement or changes one of the start time of the first blood pressure measurement and the start time of the second blood pressure measurement to provide the idle time between the first blood pressure measurement and the second blood pressure measurement.

According to the sphygmomanometer, the adjustment storage unit stores that the control unit disables one of the first blood pressure measurement and the second blood pressure measurement or changes one of the start time of the first blood pressure measurement and the start time of the second blood pressure measurement to provide the idle time between the first blood pressure measurement and the second blood pressure measurement. Therefore, when the blood pressure measurement performed at a predetermined time and the blood pressure measurement performed at a predetermined time interval from going to sleep overlap or are close to each other in the nighttime blood pressure measurement, the subject can confirm that a situation in which the blood pressure measurement is continuously performed is avoided afterwards, for example, after getting up.

In another aspect, a blood pressure measurement method of the present disclosure is performed in a nighttime blood pressure measurement mode for automatically starting blood pressure measurement according to a predetermined schedule, wherein the schedule includes a first type schedule in which blood pressure measurement is started at a predetermined time and a second type schedule in which blood pressure measurement is started at a predetermined time interval from a designated time, the blood pressure measurement method comprising:

setting the first type schedule and the second type schedule, and disabling one of first blood pressure measurement scheduled based on the first type schedule and second blood pressure measurement scheduled based on the second type schedule or changing one of a start time of the first blood pressure measurement and a start time of the second blood pressure measurement to provide idle time between the first blood pressure measurement and the second blood pressure measurement in a case where the time zone of the first blood pressure measurement and the time zone of the second blood pressure measurement at least partially overlap with each other or in a case where a time difference between the time zone of the first blood pressure measurement and the time zone of the second blood pressure measurement is equal to or less than a predetermined value.

According to the blood pressure measurement method of this disclosure, in the nighttime blood pressure measurement, when the blood pressure measurement performed at the predetermined time overlaps with or is close to the blood pressure measurement performed at the predetermined time interval from going to sleep, a situation in which the blood pressure measurement is continuously performed is avoided.

In still another aspect, a computer-readable recording medium of the present disclosure is a computer-readable recording medium non-transitorily storing a program for causing a computer to execute the blood pressure measurement method.

By making a computer read the program stored in the computer-readable recording medium according to the present disclosure and causing a computer to execute the program, the blood pressure measurement method can be implemented.

As clear from the above, according to the sphygmomanometer and the blood pressure measurement method of the present invention, a situation in which blood pressure measurement is continuously performed when blood pressure measurement performed at a predetermined time overlaps with or is close to blood pressure measurement performed at a predetermined time interval from a time of going to sleep can be avoided. Further, according to the program stored in the computer-readable recording medium of the present invention, it is possible to cause a computer to execute such a blood pressure measurement method.

It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A sphygmomanometer having a nighttime blood pressure measurement mode for automatically starting a blood pressure measurement by an oscillometric method according to a predetermined schedule, the sphygmomanometer comprising:

a cuff configured to be wound around a measurement target site;

a pump for supplying an air to the cuff to pressurize the cuff;

a valve for discharging the air from the cuff to depressurize the cuff;

a first switch for inputting a mode instruction to transition to the nighttime blood pressure measurement mode;

a display;

a programed processor; and a main body to which the programed processor, the pump and the valve are mounted, wherein the first switch and the display are arranged on a surface of the main body, the predetermined schedule includes a first type schedule in which the blood pressure measurement is started at a predetermined time during a nighttime and a second type schedule in which the blood pressure measurement is started at each start time set with a predetermined time interval during the nighttime from a designated time at which the mode instruction has been input by the first switch, in the first type schedule, a first blood pressure measurement is scheduled to have a time zone length between one minute and two minutes from the predetermined time, and in the second type schedule, a second blood pressure measurement is scheduled to have a time zone length between one minute and two minutes from each start time that is set with the predetermined time interval, the programed processor is configured to:

transition to the nighttime blood pressure measurement mode when the mode instruction is input by the first switch, initially set a time zone of the first blood pressure measurement according to the predetermined time, and initially set a time zone of the second blood pressure measurement by the second type schedule according to each start time that is set with the predetermined time interval from the designated time;

determine, prior to starting waiting for the time zones of the first blood pressure measurement and the second blood pressure measurement that have been initially set in the nighttime blood pressure measurement mode, whether or not the time zone of the first blood pressure measurement and the time zone of the second blood pressure measurement at least partially overlap with each other or whether or not a time difference between the time zone of the first blood pressure measurement and the time zone of the second blood pressure measurement is equal to or less than a predetermined value;

perform an adjustment to disable one of the first blood pressure measurement and the second blood pressure measurement or to change one of a start time of the first blood pressure measurement and a start time of the second blood pressure measurement to provide an idle time between the first blood pressure measurement and the second blood pressure measurement in a case a result of the determination is an affirmative result that the time zones partially overlap or the time difference is equal to or less than the predetermined value;

cause the display, prior to starting waiting for the time zones of the first blood pressure measurement and the second blood pressure measurement that have been adjusted, to display the start time of the first blood pressure measurement and/or the start time of the second blood pressure measurement;

subsequently wait for the time zones of the first blood pressure measurement and the second blood pressure measurement to arrive; and perform the blood pressure measurement by the oscillometric method with pressurizing the cuff by the pump and/or depressurizing the cuff by the valve during the time zones of the first blood pressure measurement and the second blood pressure measurement, respectively.

2. The sphygmomanometer according to claim 1, wherein the programed processor is configured to cause the display to display a result of each blood pressure measurement.

3. The sphygmomanometer according to claim 1, further comprising:

a second switch for inputting a shift amount to shift a start time of the blood pressure measurement, wherein the programed processor is further configured to:

cause the display to display the start time of the first blood pressure measurement and/or the start time of the second blood pressure measurement having not been subjected to the adjustment in the case where the result of the determination is the affirmative result, and perform the adjustment to provide the idle time between the first blood pressure measurement and the second blood pressure measurement by shifting one of the start time of the first blood pressure measurement and the start time of the second blood pressure measurement by using the shift amount input by the second switch.

4. The sphygmomanometer according to claim 1, further comprising:

a memory that stores a required measurement time actually required for a past blood pressure measurement, wherein the programed processor sets the time zone length of the first blood pressure measurement and the time zone length of the second blood pressure measurement based on the required measurement time required for at least a last time blood pressure measurement.

5. The sphygmomanometer according to claim 1, wherein the programed processor sets the time zone length of the first blood pressure measurement and the time zone length of the second blood pressure measurement to a certain length between one and two minutes, respectively.

6. The sphygmomanometer according to claim 1, wherein the programed processor sets the idle time to a certain length.

7. The sphygmomanometer according to claim 1, further comprising:

a memory that stores that the programed processor disables one of the first blood pressure measurement and the second blood pressure measurement or changes one of the start time of the first blood pressure measurement and the start time of the second blood pressure measurement to provide the idle time between the first blood pressure measurement and the second blood pressure measurement.

8. The sphygmomanometer according to claim 1, wherein the main body is integrally attached to the cuff, and the first switch and the display are arranged on a side of the surface of the main body farthest from the measurement target site when the cuff is wound around the measurement target site.

9. A blood pressure measurement method for automatically starting the blood pressure measurement by the oscillometric method by the sphygmomanometer according to claim 1, the blood pressure measurement method comprising, by the programed processor:

transitioning to the nighttime blood pressure measurement mode when the mode instruction is input by the first switch, initially setting the time zone of the first blood pressure measurement according to the predetermined time, and initially setting the time zone of the second blood pressure measurement according to each start time that is set with the predetermined time interval from the designated time;

determining, prior to starting waiting for the time zones of the first blood pressure measurement and the second blood pressure measurement that have been initially set in the nighttime blood pressure measurement mode, whether or not the time zone of the first blood pressure measurement and the time zone of the second blood pressure measurement at least partially overlap with each other or whether or not the time difference between the time zone of the first blood pressure measurement and the time zone of the second blood pressure measurement is equal to or less than the predetermined value;

performing the adjustment to disable one of the first blood pressure measurement and the second blood pressure measurement or to change one of the start time of the first blood pressure measurement and the start time of the second blood pressure measurement to provide the idle time between the first blood pressure measurement and the second blood pressure measurement in the case where the result of the determination is the affirmative result that the time zones partially overlap or the time difference is equal to or less than the predetermined value;

causing the display, prior to starting waiting for the time zones of the first blood pressure measurement and the second blood pressure measurement that have been adjusted, to display the start time of the first blood pressure measurement and/or the start time of the second blood pressure measurement;

subsequently waiting for the time zones of the first blood pressure measurement and the second blood pressure measurement to arrive; and performing the blood pressure measurement by the oscillometric method with pressurizing the cuff by the pump and/or depressurizing the cuff by the valve during the time zones of the first blood pressure measurement and the second blood pressure measurement, respectively.

10. A non-transitory computer-readable recording medium storing a program for causing a computer to execute the blood pressure measurement method according to claim 9.

* * * * *